United States Patent [19]

Beckman

[11] Patent Number: 5,312,394
[45] Date of Patent: May 17, 1994

[54] APPARATUS AND METHOD FOR SURGICALLY PERFORMING A FILTERING OPERATION ON AN EYE FOR GLAUCOMA

[76] Inventor: Hugh Beckman, 1972 Sherwood Glen, Bloomfield Hills, Mich. 48302

[21] Appl. No.: 693,962

[22] Filed: Apr. 29, 1991

[51] Int. Cl.$^5$ .............................................. A61N 5/06
[52] U.S. Cl. .................................... 606/6; 606/10; 606/15; 606/18; 606/171; 604/20; 604/22; 601/2
[58] Field of Search ........................................ 606/2–6, 606/10–19, 107, 171; 604/20, 22; 128/24 AA

[56] References Cited

U.S. PATENT DOCUMENTS

| | | | |
|---|---|---|---|
| 3,315,680 | 4/1967 | Silbertrust et al. | 606/4 |
| 4,445,892 | 5/1984 | Hussein et al. | 128/4 |
| 4,729,373 | 3/1988 | Peyman | 606/4 |
| 4,846,172 | 7/1989 | Berlin . | |
| 4,856,513 | 8/1989 | Muller | 606/5 |
| 4,903,695 | 2/1990 | Warner et al. | 606/4 |
| 4,917,084 | 4/1990 | Sinofsky | 606/3 |
| 5,123,902 | 6/1992 | Müller et al. | 606/6 |

*Primary Examiner*—David M. Shay
*Attorney, Agent, or Firm*—Basile and Hanlon

[57] ABSTRACT

The present invention provides an apparatus and method for performing a filtering operation for glaucoma. The apparatus is a jig comprising a base for supporting the jig on the eye. An offset aperture in the base above the cornea allows cutting of a flap in the sclera. An arm is provided for supporting an oscillating blade and fiberoptic laser assembly. The blade and laser are mounted on the arm. The arm is located in the base of the jig in a slot. To cut a flap in the sclera, the oscillating blade and laser assembly is slid along the slot in the jig, thereby creating a proper angle of dissection with the blade. After the flap is elevated, the fiberoptic laser burns a hole through the choroid layer. An egress of fluid through the hole eliminates the excess pressure in the vitreous humor.

14 Claims, 2 Drawing Sheets

APPARATUS AND METHOD FOR SURGICALLY PERFORMING A FILTERING OPERATION ON AN EYE FOR GLAUCOMA

BACKGROUND OF THE INVENTION

I. Field of the Invention

The present invention relates generally to a surgical apparatus and method for performing a filtering operation for glaucoma. More particularly, the present invention relates to a jig for supporting and guiding surgical tools, such as an oscillating blade, during a filtering operation.

II. Description of the Prior Art

A common debilitating condition experienced by predominantly older people is glaucoma, an eye disease characterized by abnormally high pressure within the eyeball resulting in partial or complete loss of vision. To alleviate this pressure increase in the vitreous humor, several surgical methods have been employed.

One such surgical method requires the initial incision of a rectangular area in the conjunctiva above the cornea to access the sclera. A surgeon would then insert a knife into the scored area and cut into the sclera, the tough white coat of the eye. This cut-away creates a flap having an integral hinge about the cornea. This flap is raised to access the trabecular meshwork layer surrounding the aqueous humor. A fiberoptic laser is used to burn a hole through the meshwork area creating a passage to the anterior chamber. Pressure is stabilized as the hole allows the egress of fluids through the hole underneath the flap and then underneath the skin of the eye. After pressure is stabilized within the eye, the flap is replaced in its original position to cover the hole and sutured. A disadvantage of this previously known method for performing a filtering operation for glaucoma is that a surgeon is required to open the conjunctiva and visualize the sclera for incision. This results in later scarring of the incision site and tends to decrease the success rate of adequate filtration of the aqueous humor.

Another method used to relieve pressure within the vitreous humor is to simply burn a hole through the sclera with a fiberoptic laser. The burning of a hole directly through the outer coatings of the eye into the aqueous humor provides an egress for the fluid without creating a flap in the sclera. A disadvantage of this previously known method is that the fluid leak may be profound and result in complications. Further, the leakage of the fluid may cause a blister in the sclera or conjunctiva which may eventually burst and create an open wound in the eye which may not heal.

SUMMARY OF THE INVENTION

The present invention provides an apparatus and method for performing a filtering operation for glaucoma which overcomes the disadvantages of the previously known methods of operation.

The apparatus of the present invention comprises a jig for supporting and guiding the surgical tools needed to perform the operation. The jig comprises a base for supporting the jig on the eye. The base follows the profile of the eye about the cornea and may be manually held in place by the surgeon or mounted on the eye by a series of suction cup apparatuses.

An offset aperture is provided in an area of the jig which rests above the cornea to allow cutting of the flap in the sclera by surgical means.

A C-shaped arm is provided for supporting the surgical tools of the present invention. The arm is provided at one end with tool support means and at the opposite end with a T-shaped flange. After the tools have been placed on the arm, the arm is then slid in a corresponding T-shaped slot provided in the base of the jig. The slot then guides the surgical tools of the present invention along a proper angle of dissection with only a small hole in the conjunctiva and the blade creating a flap in the eye and then burns a hole through the deep scleral layer. In this way, the jig guides the dissection of the sclera creating a finely cut flap. The jig provides a means for common dissection of the eye, preventing blind cutting into the eye.

The surgical tools used to perform the filtering operation comprise an oscillating sharp blade and a laser delivered through a fiberoptic. The tools are joined together to create a single apparatus supported by the arm of the jig. A hollow elongate cylinder supports a fiberoptic laser internally along a horizontal plane and an oscillating blade extending externally from the cylinder along the same horizontal plane.

In the preferred embodiment, a mirror is positioned within the cylinder at an angle to the horizontal plane for reflecting the laser beam toward the eye.

The cylindrical tool is mounted on the arm of the jig. The jig is placed on the eye and receives the arm in the base's corresponding slot. The oscillating blade is activated mechanically to cut a flap in the eye. As the arm is pushed along the slot in the base of the jig, the oscillating blade dissects an area of the sclera, creating a flap. This flap is elevated away from the eye by the blade. Once the flap is elevated, the laser is then activated. The fiberoptic is directed to the mirror and reflects down into the eye where it burns a hole in the meshwork schleral layer allowing the egress of fluids through the hole. The jig is then removed, and the flap in the sclera is sutured closed creating a seal.

By providing a jig to support and guide the surgical tools during the filtering operation, a controlled dissection of a flap in the sclera may be repetitively produced. Blind dissection into the eye is eliminated. Further, the use of an oscillating blade to perform the dissection serves to aid in the cutting of a clean flap area. The combined oscillating blade and laser surgical tool allows a surgeon to perform the filtering operation in fewer steps while providing the necessary flap for closing the hole created by the laser.

Other advantages and features of the present invention will become more apparent from the following detailed description when read in conjunction with the accompanying drawing.

BRIEF DESCRIPTION OF THE DRAWING

The present invention will be more fully understood by reference to the following detailed description of the preferred embodiment of the present invention when read in conjunction with the accompanying drawing, in which like reference characters refer to like parts throughout the views, and in which.

DESCRIPTION OF THE PREFERRED EMBODIMENT

Figure 1:
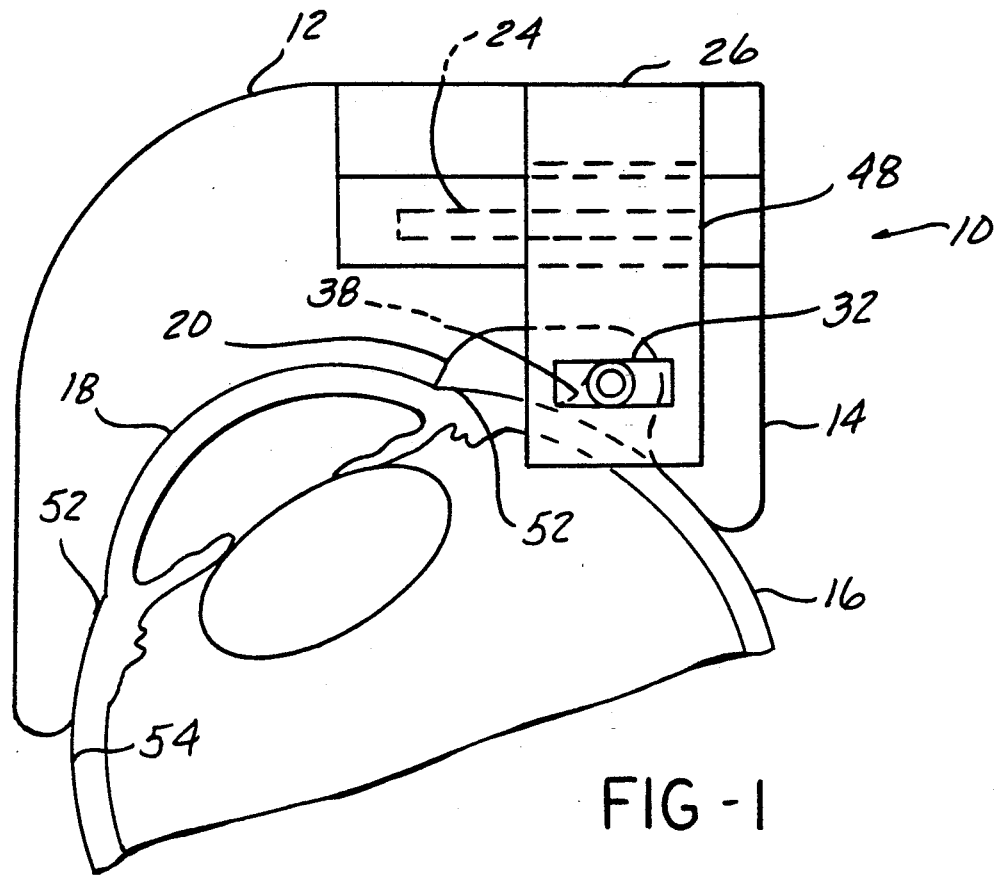
FIG. 1 is a side view illustrating a preferred embodiment of the present invention prior to dissection of the eye by the oscillating blade.
Figure 3:
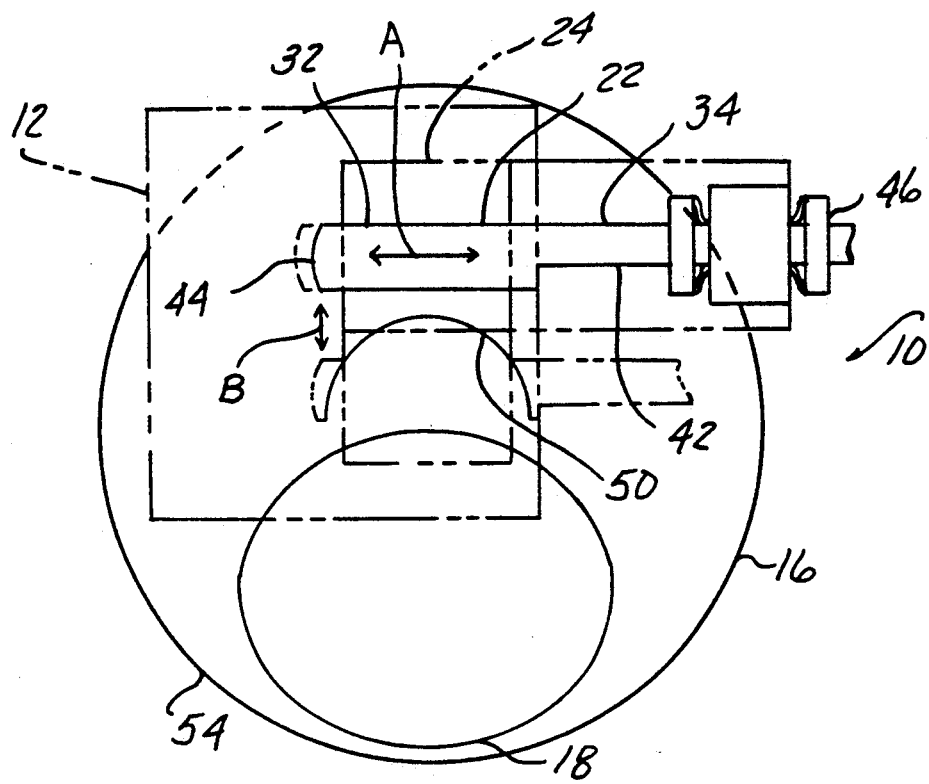
FIG. 3 is a perspective view illustrating a preferred embodiment.

With reference first to FIGS. 1 and 3, a preferred embodiment of the present invention is generally there shown at 10. A jig 12 comprises a base 14 for supporting the jig 12 on an eye 16. Base 14 has a profile corresponding to the profile of the eye 16 and seats on the eye 16 about the cornea 18.

An arcuate cut-away 20 is provided in the base 14 so that proper dissection of the eye 16 may be performed by the surgical tools generally shown at 22.

Figure 2:
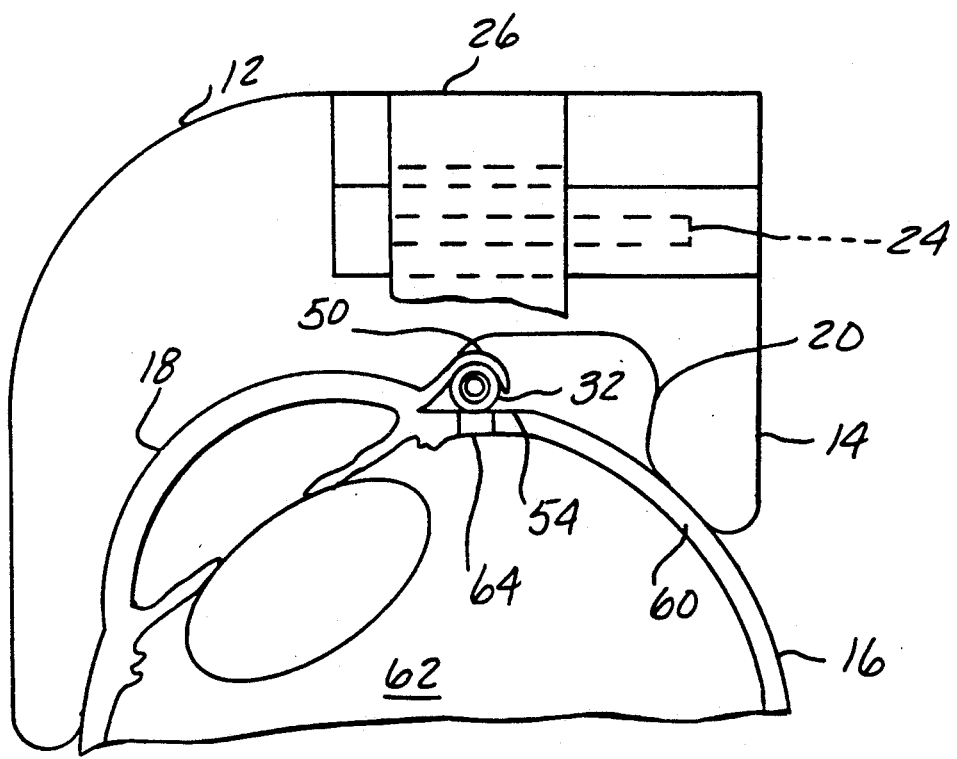
FIG. 2 is a side view illustrating a preferred embodiment of the present invention after dissection of the eye.

A T-shaped slot 24 (FIG. 4) is provided in base 14 to support arm 26. Arm 26 is comprised of a corresponding T-shaped flange 28 which may be slidably received by slot 24. Arm 26 cantilevers beyond eye 16 and provides a mount 30 for surgical tools 22. During the filtering operation, arm 26 is slid along slot 24 as best shown in FIG. 2.

Figure 4:
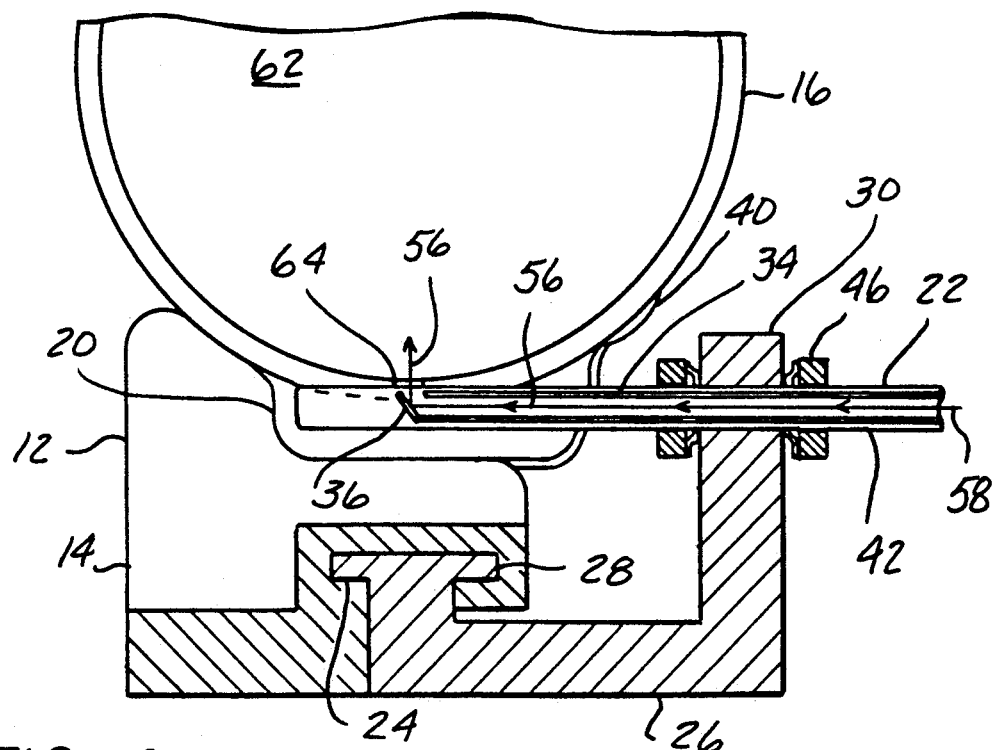
FIG. 4 is a top view of the embodiment of FIGS. 1 and 2.

With reference now to FIGS. 1 and 4, the surgical tools 22 of the present invention are there shown. The tools 22 needed to perform the filtering operation comprise an oscillating blade 32 and a laser fiberoptic 34. A reflective surface or mirror 36 may also be provided therewith for reflection of the laser fiberoptic 34.

Oscillating blade 32 is provided with an arcuate profile 38 corresponding to the arcuate cut-away 20 in base 14. The purpose of this profile will be explained in greater detail below.

With reference now to FIGS. 1 through 4, a preferred method of performing filtering operations for glaucoma using the present invention is described herewith. Jig 12, preferably formed of a lucite material, is positioned on the eye 16. The jig 12 may be held in place manually or by means of suction cups 40 (FIG. 4) during the operation.

Cylindrical housing 42 supports the laser fiberoptic 34 and mirror 36 internally while oscillating blade 32 extends externally at one end 44. Housing 42 with blade 32 are mounted to arm 26 of jig 12 by mounting means 46 such as a biased spring clamp.

Arm 26 is then placed in slot 24 at a point 48 furthest from eye 16. Oscillating blade 32 is then activated by mechanical means such as is well known in the art and oscillates along the horizontal path A. Blade 32 with laser 34 is then guided along slot 24 to dissect a flap 50 through the conjunctiva 52 and sclera 54 at a point above the cornea 18. The slot 24 assures a proper angle of dissection with the blade 32. The full stroke of the oscillating blade from its first position as shown in FIG. 1, to its final position as shown in FIG. 2, is preferably 4½ inches. As blade 32 oscillates along path A, it is moved downwardly along path B in slot 24 to cut flap 50.

Flap 50 follows the arcuate profile 38 of blade 32 and corresponding cut-away 20 in jig 12 elevating flap 50 away from the eye 16.

Mechanical means such as a foot press (not shown) activates laser fiberoptic 34. Laser beam 56 (as shown in arrows in FIG. 4) is directed to mirror 36 which is placed at an angle to horizontal plane 58 of the cylindrical housing 42. Mirror 36 is placed at such an angle within housing 42 to reflect the laser downwardly toward the eye 16. Laser 34 burns a hole through the choroid layer 60 allowing the egress of fluid forming the vitreous humor 62 through the hole 64.

Jig 12 is removed from the eye 16, and the hole 64 in the sclera 54 is sutured closed with flap 50 creating a seal.

The oscillating blade 32 of the present invention is preferably formed of stainless steel, sapphire or diamond, respectively, to create a clean line of dissection in the sclera 54. Further, laser 34 is preferably a high power, low energy cold laser such as RSP $CO_2$ laser. However, as the $CO_2$ laser is presently not available for use with a fiberoptic, a preferred embodiment of the present invention is the use of an erbium YAG laser. A second preferred method is the use of a holmium YAG laser.

It can be seen from the present invention that the jig provides a means for dissecting an eye without requiring blind cutting into the sclera by a surgeon with minimal conjunctival dissection. The slot in the jig guides the oscillating blade along a proper angle within the sclera thus eliminating the possibility of any unnecessary damage or dissection to the eye. Further, the use of an oscillating blade to perform the dissection aids in creating a clean line along the flap edges. The apparatus and method of the present invention provides a standard way of performing the filtering operation procedure while eliminating unnecessary dissection and other possible complications which may occur during the operation. The use of the jig and the oscillating blade creates the ability to perform the standard surgery on an outpatient basis with minimal dissection.

Having described my invention, however, many modifications thereto would become apparent to those skilled in the art to which it pertains without deviation from the spirit of the invention as defined by the scope of the appended claims.

I claim:

1. An apparatus for surgically performing a filtering operation on an eye for treatment of glaucoma comprising:

a jig having a base positionable on the eye and a mounting arm connected to and extending above said base; and means for surgically performing the filtering operation on the eye, said surgical filtering means slideably attached to said mounting arm and comprising an oscillating blade having an arcuate profile for supporting a section of the eye during dissection of the eye by said blade, exposing underlying ocular tissue thereby, wherein said jig has an arcuate cutout corresponding to said blade profile for receiving said dissected section.

2. The apparatus as defined in claim 1 wherein said blade comprises a stainless steel cutting edge.

3. The apparatus as defined in claim 1 wherein said blade comprises a sapphire cutting edge.

4. The apparatus as defined in claim 1 wherein said blade comprises a diamond cutting edge.

5. The apparatus of claim 1 wherein said surgical filtering means further comprises a laser fiberoptic capable of producing a hole in said exposed ocular tissue.

6. The apparatus of claim 5 wherein said mounting arm further comprises:

a first arm member terminating in a slot for receiving and guiding said oscillating blade; and a carriage device received within said slot, said carriage device comprising a flange adapted to be slidably received in said slot, a second arm member integrally attached to said flange and extending outward therefrom and a housing integrally attached to said second arm at a position distal from said flange, said housing having a horizontal axis oriented essentially parallel to a chosen incision site on the eye and containing said laser fiberoptic and said oscillating blade in operative positions essentially parallel to said horizontal axis.

7. An apparatus for surgically performing a filtering operation on an eye for glaucoma comprising:
   a base positionable on the eye;
   a jig supported on said base, said jig having an arm extending above said base, said arm terminating in a T-shaped slot; and
   means for surgically performing said filtering operation, said surgical performing means comprising:
   a) a carriage device having a T-shaped flange slideably mounted within said T-shape slot located in said arm;
   b) a hollow elongate cylindrical housing fixedly mounted to said carriage device;
   c) a laser fiberoptic and fiberoptic supported internally of said hollow cylindrical housing along a horizontal plane; and
   d) a blade extending externally from said hollow cylindrical housing along said horizontal plane, said blade comprising an arcuate profile for supporting a section of the eye during dissection of the eye by said blade;
   wherein said jig has an arcuate cut-out corresponding to said blade profile receiving said dissected section of the eye.

8. The apparatus as defined in claim 7 wherein said carriage device slidable along said slot to guide said dissection of the sclera of the eye by said blade.

9. The apparatus as defined in claim 7 including a laser coupled to said laser fiberoptic wherein said laser is an erbium YAG laser.

10. The apparatus as defined in claim 7 including a laser coupled to said laser fiberoptic wherein said laser is a holmium YAG laser.

11. The apparatus as defined in claim 7 wherein said blade is an oscillating blade having a stroke of about $4\frac{1}{2}$ inches between an initial position and a final position.

12. The apparatus as defined in claim 7 wherein said blade comprises a stainless steel cutting edge.

13. The apparatus as defined in claim 7 wherein said blade comprises a sapphire cutting edge.

14. The apparatus as defined in claim 7 wherein said blade comprises a diamond cutting edge.

* * * * *

UNITED STATES PATENT AND TRADEMARK OFFICE
CERTIFICATE OF CORRECTION

PATENT NO. : 5,312,394
DATED : May 17, 1994
INVENTOR(S) : Hugh Beckman

It is certified that error appears in the above-indentified patent and that said Letters Patent is hereby corrected as shown below:

Column 5, line 22, please delete "and" and insert --said--.

Signed and Sealed this

First Day of November, 1994

Attest:

BRUCE LEHMAN

Attesting Officer

Commissioner of Patents and Trademarks